Figure 1:
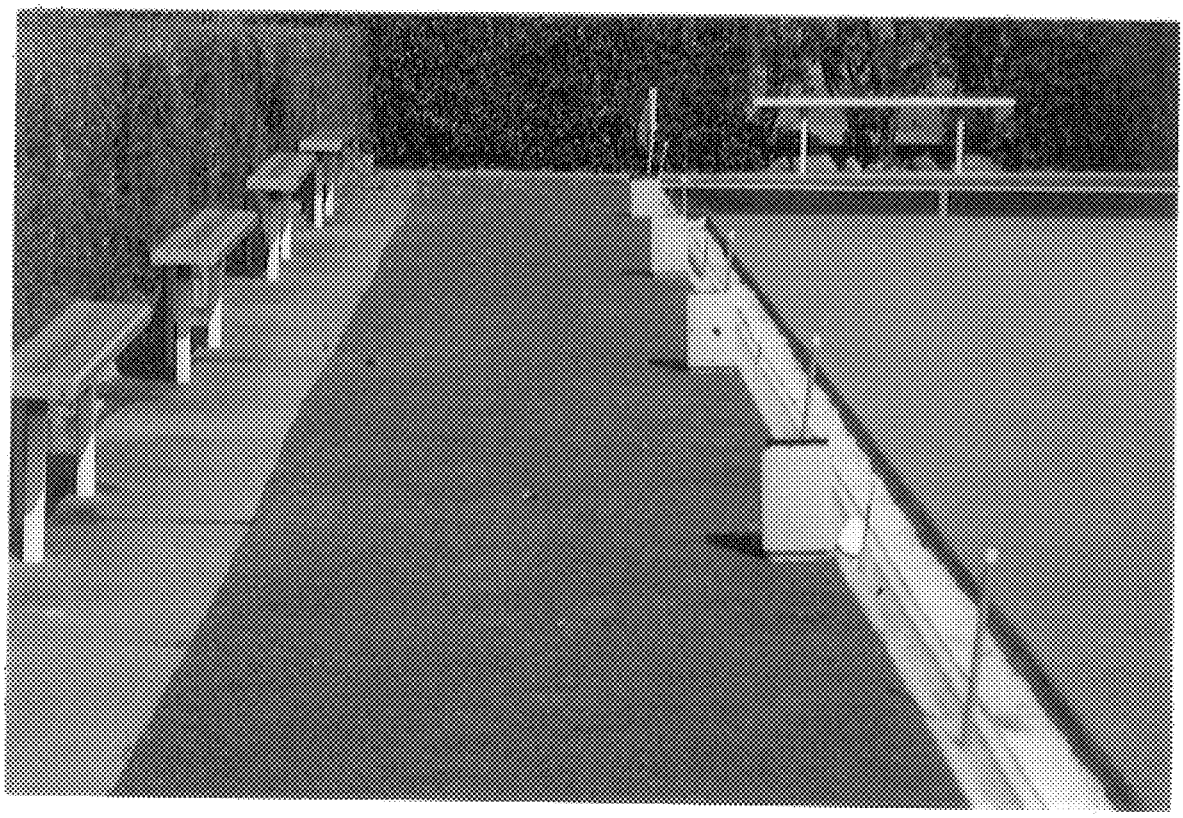

US00PP11181P

United States Patent [19]

Riley

[11] Patent Number: Plant 11,181

[45] Date of Patent: Jan. 18, 2000

[54] *CYNODON DACTYLON* PLANT NAMED 'RILEY'S SUPER SPORT'

[76] Inventor: Rodney J. Riley, 49 Iris Street, Guilford, New South Wales, 2161, Australia

[21] Appl. No.: 08/903,947

[22] Filed: Jul. 31, 1997

[51] Int. Cl.[7] ..... A10H 5/00

[52] U.S. Cl. ..... Plt./389

[58] Field of Search ..... Plt./90, 389

[56] References Cited

PUBLICATIONS

A.S. Hitchcock , Manual of the Grasses of the United States, vol. 1, Dover Publications, Inc., New York, pp. 503–504, 1971.

GTITM UPOVROM Citation for 'Riley's SuperSport' as per AU PBR 95127, Feb. 28, 1997.

*Primary Examiner*—Howard J. Locker
*Assistant Examiner*—Kent L. Bell
*Attorney, Agent, or Firm*—Christie, Parker & Hale, LLP

[57] ABSTRACT

A new variety of *Cynodon dactylon* exhibiting prostrate growth, short internode length, minimal seed head production and deep green coloration.

4 Drawing Sheets

BACKGROUND OF THE INVENTION

The present invention relates to a new and distinct *Cynodon dactylon* variety.

The new variety is the result of a spontaneous mutation of the *Cynodon dactylon* variety 'Greenlees Park' (unpatented) and was propagated vegetatively through four generations. The varietal denomination of the new variety is 'Riley's Super Sport'.

There is an ongoing need in the United States for turf grass varieties which are hard wearing, low in maintenance and which provide good ground cover and attractive grass color. Such varieties find particular use on playing fields, golf courses, bowling greens, parks, as well as in domestic and commercial settings.

The parent of 'Riley's Super Sport', 'Greenlees Park', is widely used in the United States, such as in the California area, on golf courses at tees and on fairways. As described hereinafter 'Riley's Super Sport' is an advantageous turf grass species in many respects over and above commercial turf grass species.

SUMMARY OF THE INVENTION

The new variety of *Cynodon dactylon*, 'Riley's Super Sport', exhibits a very prostrate growth habit thereby having minimal vertical growth (that is, very prostrate growth habit), extensive leaf production, short internode length, very low seed head production, and deep green coloration, amongst other characteristics herein described which distinguish the subject variety from presently available commercial turf grass varieties. Under moderate climatic conditions such as coastal areas of California, green color quality can be maintained throughout the year. The new variety is vegetatively propagated from sod, plugs, tillers or stolons and rhizome pieces. Asexual propagation by rhizomes and tillers at the Australian Turf Grass Research Institute in Sydney, New South Wales, Australia has demonstrated that the combination of characteristics of the new variety are transmitted through succeeding propagations.

'Riley's Super Sport' differs from 'Greenlees Park' in having a very prostrate growth habit, extensive leaf production, leaf dimensions, leaf color, short internode length, and minimal seed head production.

BRIEF DESCRIPTION OF ILLUSTRATIONS

The accompanying illustrations show typical specimens of the vegetative growth of the new variety.

FIG. 1: shows turf appearance of the new variety in use at bowling green, with the bank (left hand side of the Figure) cut at 6 mm height, and the green (right hand side of the Figure) cut at 1 mm height.

Figure 2:
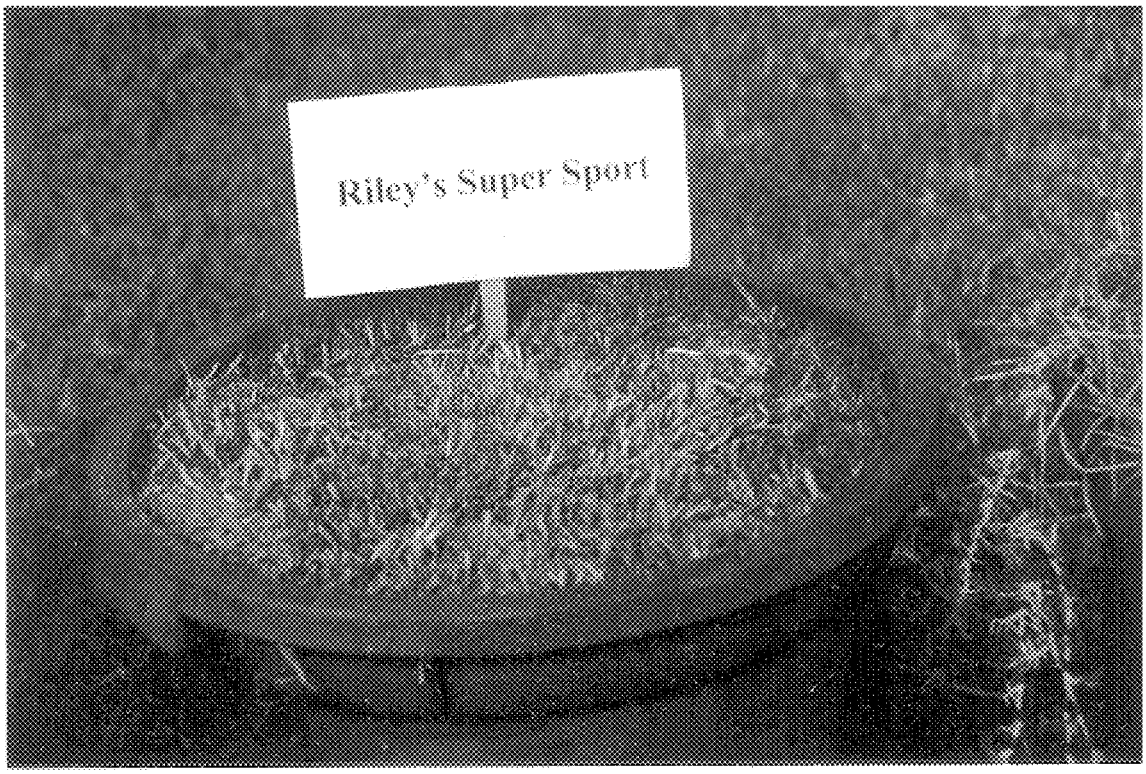

FIG. 2: shows six months growth of the new variety cultivated in plant pots.

Figure 3:
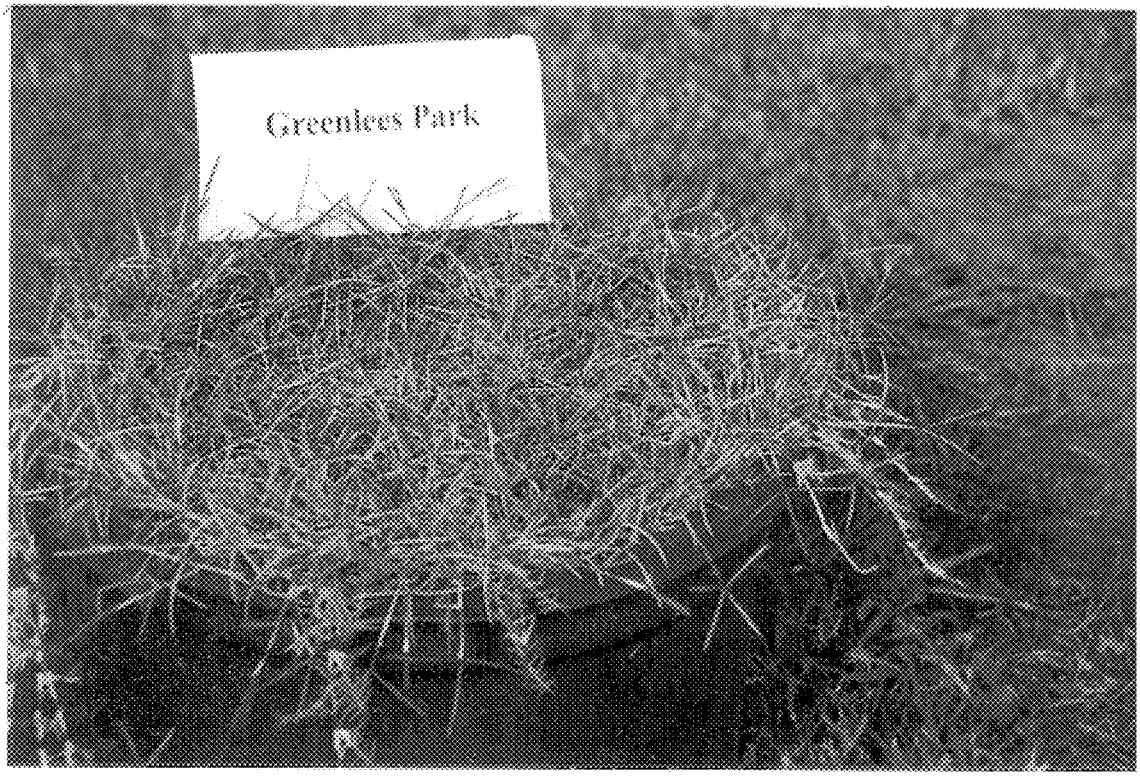

FIG. 3: shows six months growth of the comparative variety 'Greenlees Park' cultivated in plant pots.

Figure 4:
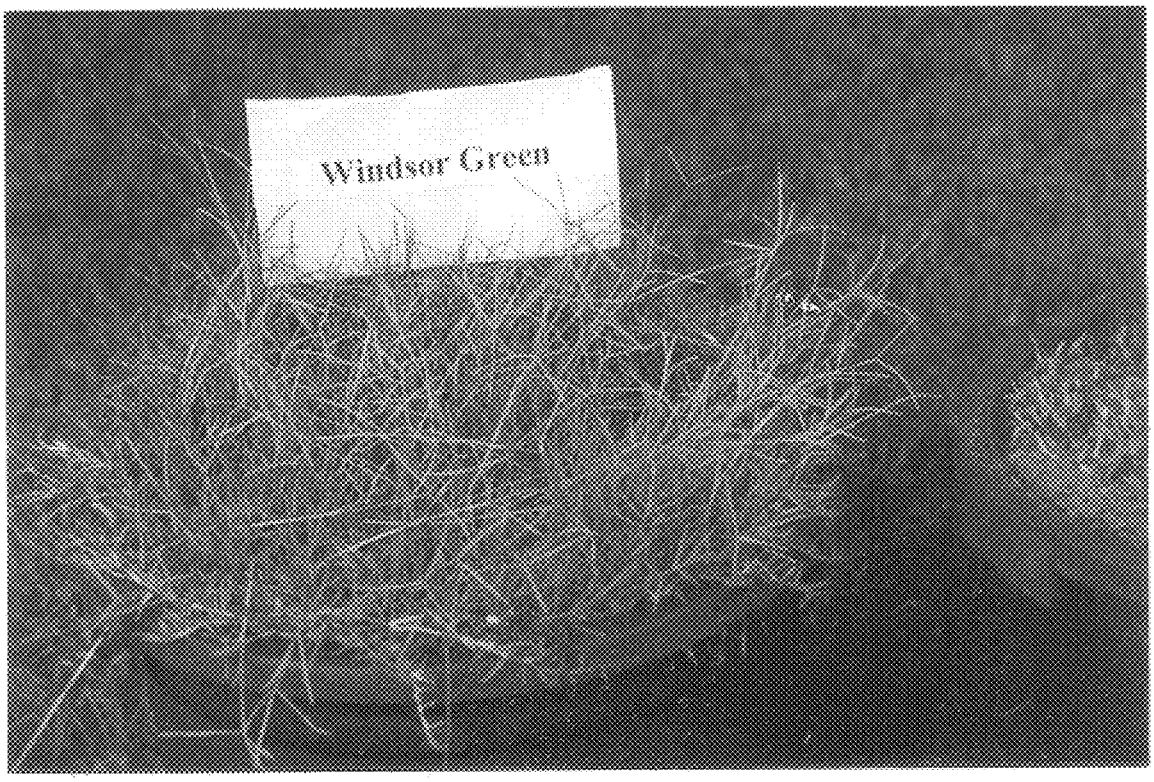

FIG. 4: shows six months growth of the comparative variety 'Windsor Green' (unpatented) cultivated in plant pots.

Figure 5:
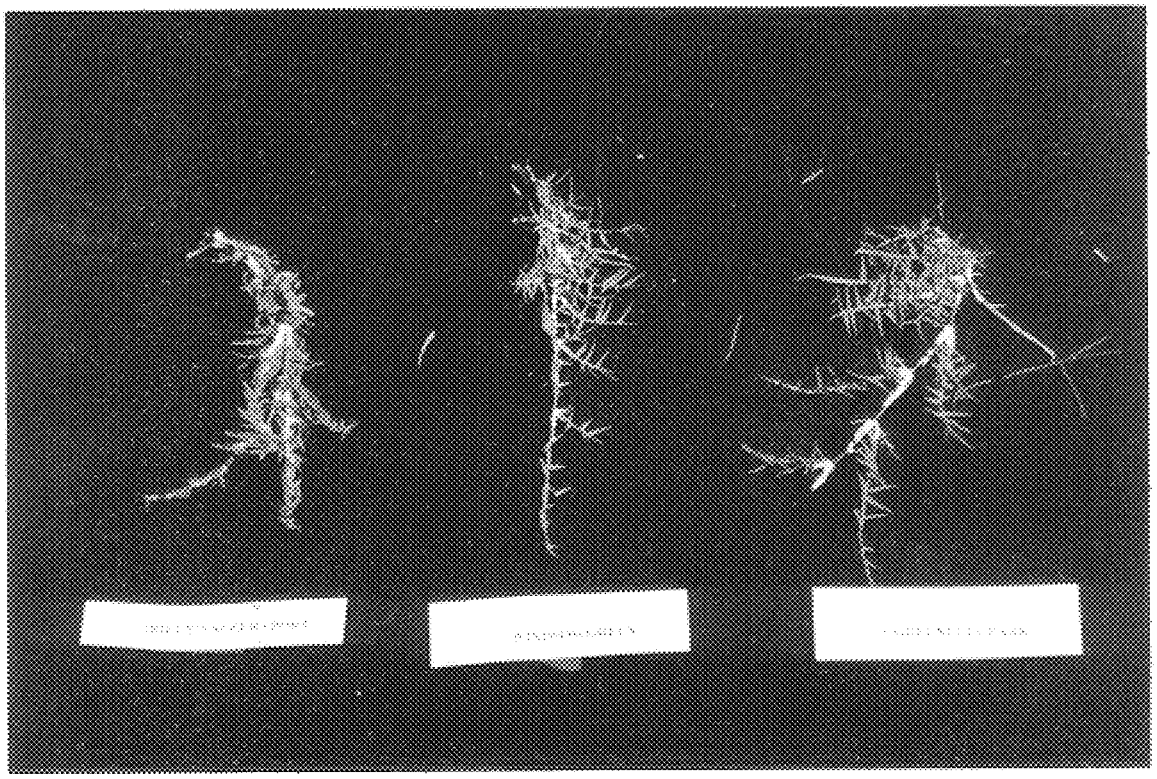

FIG. 5: shows a close up of isolated stolons of the new variety and comparative varieties 'Windsor Green' and 'Greenlees Park'

Figure 6:
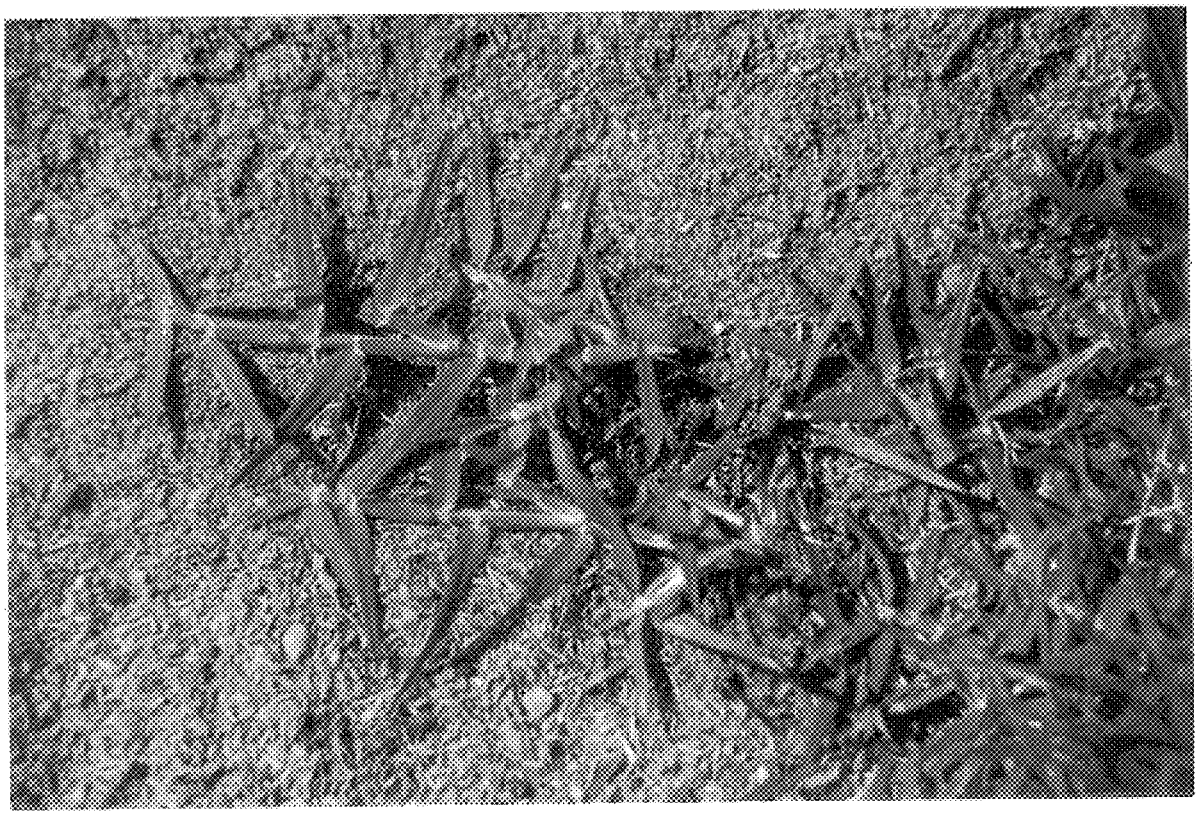

FIG. 6: shows the growth habit of the new variety.

DESCRIPTION OF THE NEW VARIETY

The description of color is by reference to The Royal Horticultural Society Colour Chart.

The new variety 'Riley's Super Sport' is a spontaneous mutation of the variety 'Greenlees Park'. It forms a dense turf that spreads by way of tillers, stolons and rhizomes.

The new variety has a very prostrate growth habit with a medium lateral extension rate and high node density.

Leaf blades are of yellow green coloration, R.H.S. 147A. Mean leaf length is 8 mm, mean leaf width is 1.7 mm and the mean leaf length:width ratio is 5/1.

Stolons of 'Riley's Super Sport' are red/purple, are of high density, with a short internode length having a mean of 13.6 mm.

Winter growth of 'Riley's Super Sport' is low, with an unmown height over winter having a mean of 8 mm.

The new variety is vegetatively propagated from sod, plugs or stolon or rhizome pieces. It performs best in full sun, but also grows well in shade. It is hard wearing and has an easily controllable mat density which is responsive to mowing management in order to provide a hard surface, for use such as in bowling greens, or a soft surface for use such as in parks, on golf fairways, or in domestic situations. In drought conditions the new variety recovers quickly on application of water. As a consequence the turf formed from the new variety is suitable for situations requiring a durable, high quality lawn that is tolerant of heat and drought stress. As previously mentioned, such applications include parks, golf courses, bowling greens, domestic lawns, and public planting areas. The accompanying illustrations serve to illustrate the distinctive features of the new variety. As can be seen from FIG. 1 the variety can be finely cut, such as 1 mm height, to provide a dense mat of prostrate growth habit for use as a bowling or putting green, or cut at a greater height, such as 6 mm to provide a durable walking surface, such as the verge of a bowling green, golf fairway and many other such applications. FIGS. 2 to 4 show growth of the new variety 'Greenlees Park' and 'Windsor Green' after six months in plant pots, cultivated in Sydney, New South Wales, Australia, under ambient conditions. As is clearly evident from these figures, the new variety shows compact growth with little vertical extension. The new variety is a low lying grass in contrast with the marked vertical extension of the comparative varieties 'Greenlees Park' and 'Windsor Green' . FIG. 5 shows stolons of the new variety, 'Greenlees Park' and 'Windsor Green'. The new variety is clearly distinguished from the comparative varieties on the basis of internode length (much shorter as shown) with consequent leaf density. FIG. 6 shows the morphology of the new variety in vivo, that is, growing in the ground. The principal features of stolon, leaf and internode length are clearly observable.

To further illustrate the differences between the new variety 'Riley's Super Sport' and the variety 'Greenlees Park' tests were conducted at the Australian Turf Grass Research Institute, New South Wales, from October 1995 through to March 1996. Thirty stolons were used to establish each grass variety in sandy soil in pots in the open using standard turf grass management practices. A hundred samples of each variety were measured for internode length, stolon thickness, leaf length and width. Twenty measurements were made for unmown sward, and ten grid counts for seed head density. The results of these evaluations are shown in Table 1. In this test the variety 'Windsor Green', another turf grass variety, was also included.

Statistical differences among the cultivars were determined according to standard statistical tests. 'Riley's Super Sport' had a very prostrate growth habit compared with a bunched growth habit of 'Windsor Green' and a prostrate growth habit of 'Greenlees Park'. Node density of 'Riley's Super Sport' was very high (mean internode length being 13.6 mm) compared to a high node density of 'Windsor Green' (mean internode length 40.2 mm), and a medium to high medium node density of 'Greenlees Park' (mean internode length 28.9 mm). The significant difference in internode length of the new variety, compared to the comparative varieties results in a greater abundance of leaf (as leaves are produced at nodes) and hence density of ground cover.

The mean uncut sward height (11.7 mm), leaf length (8 mm), leaf width (1.7 mm), and leaf length:width ratio (5/1) shown in Table 1 clearly differentiates 'Riley's Super Sport' from the varieties 'Windsor Green' and 'Greenlees Park'. This combination of characteristics associated with high density, short internode length (mean 13.6 mm) stolons provides a high density turf of pleasant appearance providing excellent ground cover with minimal vertical growth.

Seed head production was extremely low, having a mean number of seed heads being $^{0.2}/_{100}$ cm2 for the subject variety, compared to a mean of $^{2.5}/_{100}$ cm 2 for 'Windsor Green', and a mean of $^{4.0}/_{100}$ cm2 for the variety 'Greenlees Park'. The very low seed head production of the variety 'Riley's Super Sport' gives an attractive appearance of the turf and decreases the need for mowing to remove seed heads. Where seed heads are allowed to produce flowers, the anther color is red purple (64B). 'Riley's Super Sport' is a turf grass variety of *Cynodon dactylon* having the adorementioned features which distinguish it from the variety 'Greenlees Park'. The subject variety has additional characteristics of: leaves folded in bud shoot; short leaf blade (8mm), keeled and acuminate at the tip; leaf blade margin ciliate; absence of auricle; very low seed heads (0–$^{2}/_{100}$ $cm^2$) with generally 3 to 5 spikes which are up to 2.5cm long; spikelets up to 2mm long; stolons present with a width of 1.3mm; rhizomes present with a width a 1.6mm. The subject variety contains other standard characteristics of *Cynodon dactylon* varieties which do distinguish it from, and are common to, other *Cynodon dactylon* varieties, particularly culm, glume, sheath and lemma.

Lateral extension rate of 'Riley's Super Sport' was measured against 'Greenlees Park' over 14 days. Measurements were taken on pioneer stolons of 5cm length growing from 100mm diameter plugs. The area around the plug was divided into 8 equal sectors. The longest stolon in each sector was measured. Four replicate plugs of each grass were used in measurements. Mean lateral extension rate is as follows:

| Grass | Lateral extension rate (cm) |
|---|---|
| 'Riley's Super Sport' | 10.4 |
| 'Greenlees Park' | 13.5 |

The new variety exhibits no unusual resistance or susceptibility to pests or diseases as compared to the species.

TABLE 1

| | Cynodon Varieties | | |
|---|---|---|---|
| | Riley's Super Sport' | Windsor Green' | 'Greenlees Park' |
| PLANT | | | |
| habit | very prostrate | bunched | prostrate |
| lateral extension rate | medium | slow to medium | medium to high |
| node density | very high | high | medium |
| mean internode length | 13.6 mm | 40.2 mm | 28.9 mm |
| UNCUT SWARD HEIGHT (mm) | | | |
| mean | 11.7 | 87.2 | 21.8 |
| std deviation | 0.95 | 8.52 | 2.87 |
| LSD/sig | 8.40 | $p \leqq 0.01$ | $p \leqq 0.01$ |
| LEAF LENGTH | | | |

TABLE 1-continued

| | Cynodon Varieties | | |
|---|---|---|---|
| | Riley's Super Sport' | Windsor Green' | 'Greenlees Park' |
| (mm) | | | |
| mean | 8.0 | 14.7 | 11.7 |
| std deviation | 0.29 | 1.13 | 0.34 |
| LSD/sig | 1.58 | p ≦ 0.01 | p ≦ 0.01 |
| LEAF WIDTH (mm) | | | |
| mean | 1.7 | 1.3 | 1.8 |
| std deviation | 0.03 | 0.04 | 0.06 |
| LSD/sig | 0.07 | p ≦ 0.01 | p ≦ 0.01 |
| LEAF LENGTH:WIDTH RATIO | | | |
| mean | 5/1 | 12/1 | 7/1 |
| std deviation | 0.2 | 1.7 | 0.1 |
| LSD/sig | 1.41 | p ≦ 0.01 | p ≦ 0.01 |
| LEAEF COLOR | | | |
| (RHS) | yellow green | green 137B | yellow green |
| colour | 147A | | 147B |

TABLE 1-continued

| | Cynodon Varieties | | |
|---|---|---|---|
| | Riley's Super Sport' | Windsor Green' | 'Greenlees Park' |
| SEED HEADS/100 cm2 | | | |
| mean | 0.2 | 2.5 | 4.0 |
| std deviation | 0.4 | 1.1 | 0.9 |
| LSD/sig | 1.13 | p ≦ 0.01 | p ≦ 0.01 |

As mentioned above 'Riley's Super Sport' is vegetatively propagated from sod, plugs, tillers or stolons and rhizome pieces. The new variety has wide application due to its desirable properties herein described.

I claim:

1. A new and distinct variety of *Cynodon dactylon* plant named 'Riley's Super Sport', substantially as described and illustrated.

* * * * *